(12) United States Patent
Takahashi et al.

(10) Patent No.: US 6,312,943 B1
(45) Date of Patent: Nov. 6, 2001

(54) SAMPLE PREPARATION APPARATUS AND SPRAY APPARATUS FOR SAMPLE PREPARATION

(75) Inventors: Toshihiro Takahashi, Yaizu; Yoshio Monji, Kawachinagano, both of (JP)

(73) Assignees: Sapporo Breweries Ltd.; Nihon Mykrolis K.K., both of Tokyo (JP)

( * ) Notice: Subject to any disclaimer, the term of this patent is extended or adjusted under 35 U.S.C. 154(b) by 0 days.

(21) Appl. No.: 09/349,727

(22) Filed: Jul. 8, 1999

(30) Foreign Application Priority Data

Jul. 9, 1998 (JP) .................................................. 10-194608
Jul. 9, 1998 (JP) .................................................. 10-194609

(51) Int. Cl.[7] .............................. C12M 1/36; C12Q 1/24
(52) U.S. Cl. ..................................... 435/286.4; 435/287.1; 435/287.9; 435/30
(58) Field of Search .............................. 435/8, 30, 286.3, 435/286.4, 287.1, 287.3, 287.9, 288.7, 808; 436/174, 177

(56) References Cited

U.S. PATENT DOCUMENTS 3,940,250   2/1976  Plakas et al. .
4,142,859 * 3/1979  Shaffer .
4,401,889 * 8/1983  Buus et al. .
4,795,612 * 1/1989  Keller .
5,366,867 * 11/1994 Kawakami et al. .
5,538,688 * 7/1996  Tezuka et al. .

FOREIGN PATENT DOCUMENTS 2-51063      2/1990  (JP) .
4-30798      2/1992  (JP) .
08-23962  *  1/1996  (JP) .
WO 92/14838  9/1992  (WO) .

* cited by examiner

Primary Examiner—William H. Beisner
(74) Attorney, Agent, or Firm—Oblon, Spivak, McClelland, Maier & Neustadt, P.C.

(57) ABSTRACT

A sample preparation apparatus for preparing a sample to be used for detecting specimens such as microorganisms isolated on a filter so as to enumerate microorganisms in the sample has a turntable on which multiple sample bases are formed, a filter insertion unit, an extractant spray apparatus, a luminescent reagent spray apparatus and a filter removal unit, disposed in order along a periphery of the turntable in a direction of rotation of the turntable. By eliminating the need to move filters between processing operations as well as any special skill required in the spraying of the extractant and reagent, the sample preparation apparatus can provide accurate microorganism counts quickly and efficiently.

13 Claims, 15 Drawing Sheets

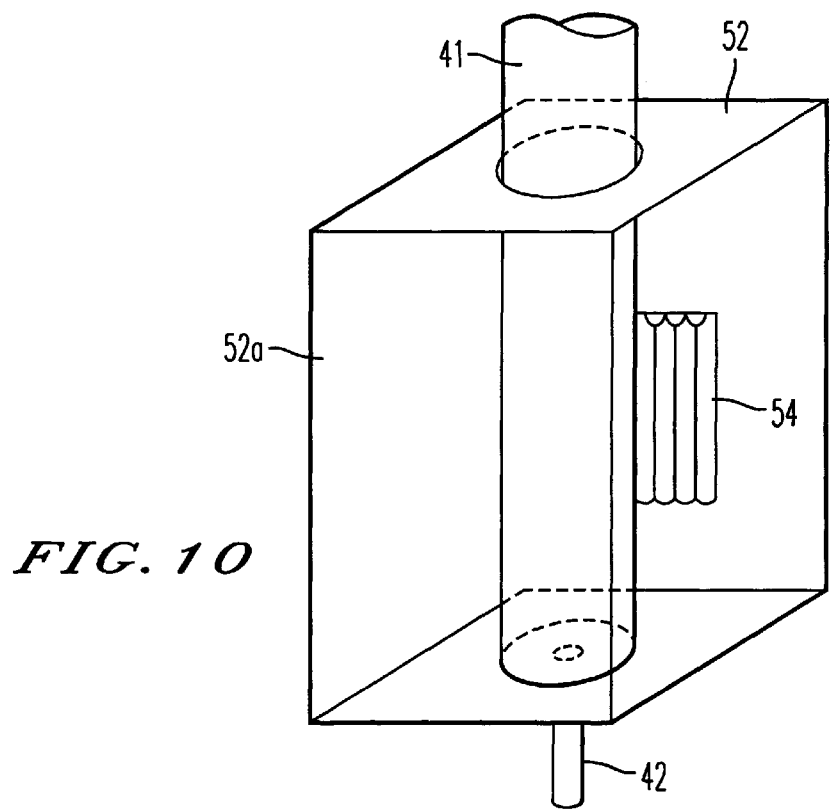
FIG. 10
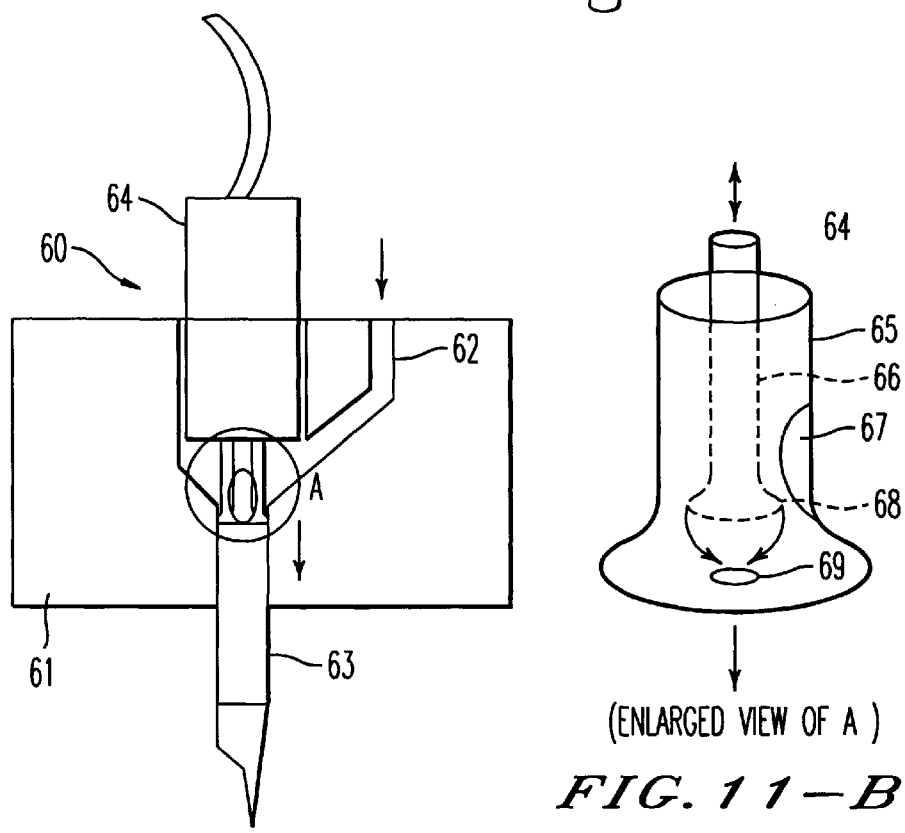
FIG. 11-A
FIG. 11-B
(ENLARGED VIEW OF A)

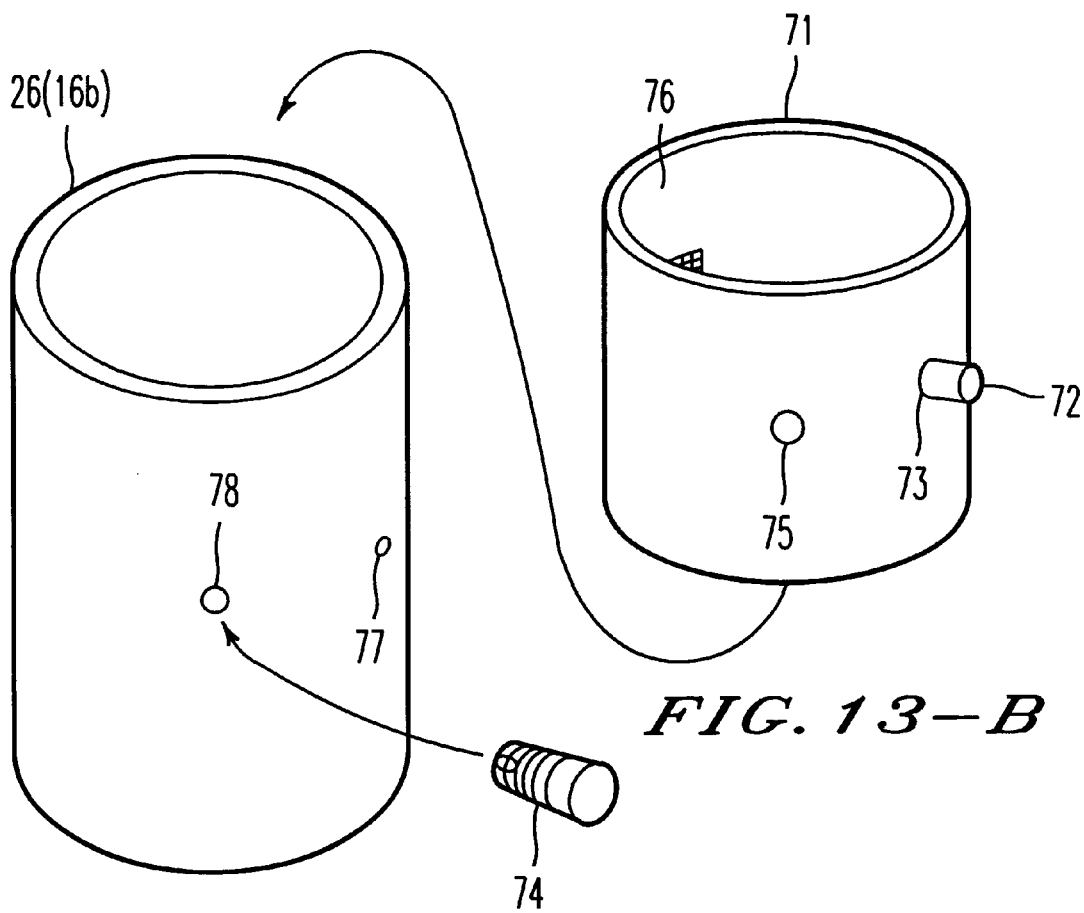
*FIG. 13-A*
*FIG. 13-B*
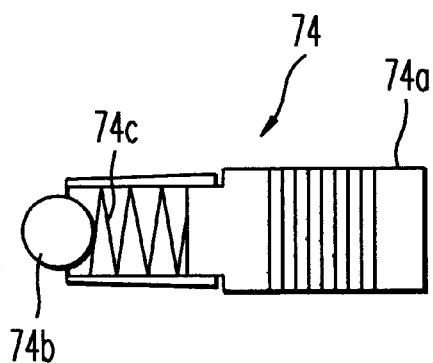
*FIG. 13-C*

SAMPLE PREPARATION APPARATUS AND SPRAY APPARATUS FOR SAMPLE PREPARATION

BACKGROUND OF THE INVENTION

1. Field of the Invention

This invention relates to an apparatus for the preparation of samples to be used for inspecting or observing a specimen isolated on a filter and sprayed with reagent by spraying a reagent on to a filer on which specimen has been isolated.

And further, the present invention relates to an apparatus for the production of samples to be used in order to measure the number of microorganisms present in the water, raw materials, semi-processed goods and other products used in the food, pharmaceutical, cosmetics, electronics and other industries, and more particularly, to a spraying apparatus for preparing samples by spraying an extractant and/or a reagent onto a filter on which the microorganisms have been isolated.

2. Description of the Related Art

Preparation of samples is performed by isolating a specimen on a filer and spraying reagent onto a filter on which the specimen is isolated when the interaction or reaction between the specimens and a reagent is observed or when the number of the isolated specimens is measured.

For example, in the food and beverage industries, as well as the cosmetics and electronics industries, the need to measure the level of microorganisms present during the production process and in the finished product is critical. Conventionally, such so-called plate counts have been performed using the agar plate method. However, in recent years a faster means of obtaining the plate count has been sought, leading to the development and use of apparatuses that skillfully combine membrane filtration, biolumines-cence technology and weak-light spots detection techniques.

Apparatuses like that described above typically operate in the following manner: A specimen is filtered by and isolated on a membrane filter. The specimen is then sprayed with an extractant and then a luminescent reagent. A highly sensitive system then counts the number of luminescent bright spots, from which the plate count is derived. So-called rapid microorganism detection systems (RMDS) employing the method described above to determine the amount of microorganisms present in a specimen are currently on the market and presently being used, and are faster than the conventional agar plate method.

Generally, these RMDS operate by filtering and isolating an appropriate amount of microorganisms on a filter according to whether the specimen is to be diluted or is to be used in bulk. At that time the microorganisms are dispersed across the surface of the filter by holding the filter as level as possible. The microorganisms so isolated are the processed and transpired with alcohol or a variety of organic solvents used in the smallest possible amounts to extract the adenosine triphosphate (ATP) an so fix the ATP at or near the positions at which the host microorganisms have been isolated. If a solution containing a luminescent reagent composed of luciferin and the luminescent enzyme luciferase is then supplied the action of normally co-existent magnesium and ambient enzymes give off light. As with the solvents these reagents too, are used in the smallest possible amounts so that, by transpiration of the luminescent reagent solvent the luminescent points remain at or near the isolate microorganisms. The number of microorganisms present can then be calculated by counting the number of luminescent points. For those microorganisms from which the amount of ATP extracted from the microorganism is small and the luminescent points are indistinct the amount of ATP extracted is boosted by a short period of culturing in an a agar culture medium after dispersal and isolation on the filter.

Nevertheless, these RMDS are not free of problems. Specifically, these systems require that the membrane filter on which the sample is isolated be supported by a supporting means such as a carrier, the membrane filter sprayed with an adenosine triphosphate (ATP) extractant and a luminescent reagent and then positioned at a detector. In order to obtain a plate count efficiently, these systems must use the smallest possibile amount of ATP extractant and luminescent reagent applied simply, accurately and quickly. That is, applying more than the required amount of ATP extraction fluid either dilutes any ATP extracted or causes the extracted ATP to disperse widely, resulting in poor lighting and/or blockage of luminescence by the residual extractant.

In order to avoid or eliminate these problems substantial time and effort must be spent on the delivery of the extractant to the sample. In this respect similar problems also attend the delivery of the luminescent reagent, with the added consideration that the luminescent reagent used herein is not easy to obtain. As a result, it is commercially vital that only the minimum effective amount of luminescent reagent be used. Accordingly, the development of a sample preparation apparatus capable of accurately and efficiently delivering only these minimum effective amounts of extractant and luminescent reagent is desirable.

Separately, the preparation of the sample also require many steps, all of which it is desirable to automate to the extent possible. Up to now efforts have been made to automate portions of the sample preparation process though so far with only limited success. In particular, the movement of the filter between steps and the replacement of the filter itself require considerable skill and leave room for improvement. For example, the first drying, extraction processing, second drying and luminescent reagent processing are all steps which must be performed manually. Accordingly, processing a large volume of samples requires a great deal of time, which time also varies with the level of skill of the operator. Additionally, the filter may be contaminated by human hands during transport of the carrier or even dropped, thereby impairing the accuracy of the measurement. When conducting inspections prior to shipping food, for example, a delay in measurement can delay the entire shipment.

Additionally, the luminescent reagent spray apparatus used in the process of preparing a sample using the sample preparation apparatus must constantly be kept clean and free of contamination, and therefore it is necessary that the apparatus have a structure that allows easy cleaning of the cylinder that composes the spraying apparatus.

Additionally, the luminescent reagent to be sprayed must constantly be kept at a low temperature in order to maintain its effectiveness, and accordingly, the reagent container is usually covered by a cooling device. However, such an arrangement poses the problem of making it impossible to tell how much reagent remains available. Moreover, although it is desirable that human intervention in the preparation of the sample be kept to a minimum and that the process therefore be automated to the extent possible, it is still necessary, for example, to accurately gauge the state of the reagent spray during delivery to the sample.

SUMMARY OF THE INVENTION

Accordingly, it is an object of the present invention to provide a sample preparation apparatus in which the problems described above are solved, by providing a sample preparation apparatus that requires a minimum of human intervention in order to operate, reduces the frequency of occurrence of breakdowns and shortens operating time.

The above-described object of the present invention is achieved by providing a sample preparation apparatus for preparing a sample to be used for inspecting specimens isolated on a filter, comprising:

a turntable on which a plurality of sample bases are formed; and a filter insertion unit, a reagent spray apparatus and a filter removal unit, disposed in order along a periphery of the turntable in a direction of rotation of the turntable.

Additionally, the above-described object of the present invention is achieved by providing a sample preparation apparatus for preparing a sample to be used for enumerating microorganisms isolated on a filter, comprising:

a turntable on which a plurality of sample bases are formed; and a filter insertion unit, an extractant spray apparatus, a luminescent reagent spray apparatus and a filter removal unit, disposed in order along a periphery of the turntable in a direction of rotation of the turntable.

According to the sample preparation apparatus described above, each spraying apparatus is operated automatically so that, by simply setting the filter on the sample base from the filter insertion unit, the steps of drying the filter, spraying the extractant on the sample, drying the extractant and spraying the luminescent reagent on the sample can all be conducted without human intervention. Accordingly, no particular skill is required for movement of the filter between steps or for operation of the spraying apparatuses, and thus these processes can be conducted simply and quickly.

Additionally, the above-described object of the present invention is also achieved by a spraying apparatus for preparing a sample for measuring an amount of specimens by spraying a reagent on a filter on which the specimens are isolated, the spraying apparatus comprising:

a sample base mounted on a turntable, the sample base mounting the membrane filter;

a cylinder for spraying a reagent, the cylinder positioned above the turntable and supported on a drive unit so as to be movable in a vertical direction;

a reagent supply unit for supplying luminescent reagent to the cylinder, the reagent supply unit mounted on top of the cylinder;

a fluid supply unit supported on a vibrating means and mounted within the cylinder; and a suction unit mounted on the bottom of the sample base.

According to the sample preparation apparatus described above, the filter can be accommodated in a sealed state within the cylinder and thus the sample can be sprayed with reagent without the reagent spray being dispersed externally. As a result, even trace amounts of dispersed, rising spray are retained by suction from the bottom of the filter and by the cover at the top of the filter.

BRIEF DESCRIPTION OF THE DRAWINGS

Other objects, features and advantages of the present invention will become more apparent from the following detailed description when read in conjunction with the accompanying drawings, in which:

FIG. 10 is a diagram of a cooling chamber;

FIG. 11 is a diagram of a flow control unit;

FIG. 13 is a diagram for explaining a structure to be mounted on a sensor unit and sensor unit cylinder;

DESCRIPTION OF THE PREFERRED EMBODIMENTS

A detailed description will now be given of an embodiment of the present invention with reference to the accompanying drawings. As an initial matter, a description will be given of the overall composition of a plate count detection system for detecting a plate count using a sample prepared by using the spraying apparatus of the present invention.

Broadly speaking, the plate count detection system comprises three distinct stages or operations. The first operation involves filtering the specimen with a membrane filter and isolating the live cells on the filter. It should be noted that it is desirable that the membrane filter used here be a polycarbonate filter to which is fitted doughnut-shaped frame. That is, the filter is made to have a certain degree of rigidity so as to minimize bending and breakage and thereby improve operational efficiency. In addition, in the reagent processing operation and measuring operation which follow the above-described filtering operation, the need for mounting the filter on a carrier and transporting the filter thereby is eliminated, thus making possible a considerable improvement in the ease with which the apparatus is operated. Moreover, by using a polycarbonate filter the live cells in the specimen can be efficiently concentrated and uniformly dispersed. As a result, dilution of the ATP extract obtained in the succeeding operation can be prevented.

The second operation involves delivering an extractant to each of the filters in order to extract the ATP in the live cells isolated on the membrane filter in the operation described above, after which a luminescent reagent containing luciferin and luciferase is delivered in order to create luminescence. The reagent used in this operation is an RMD reagent sold by Nihon Millipore as a kit. It should be noted that, in order to effectively reactively illuminate the ATP and luminescent reagent on the microorganisms isolated on the filter, the above-described reagent must be sprayed evenly and in an appropriate amount.

Figure 1:
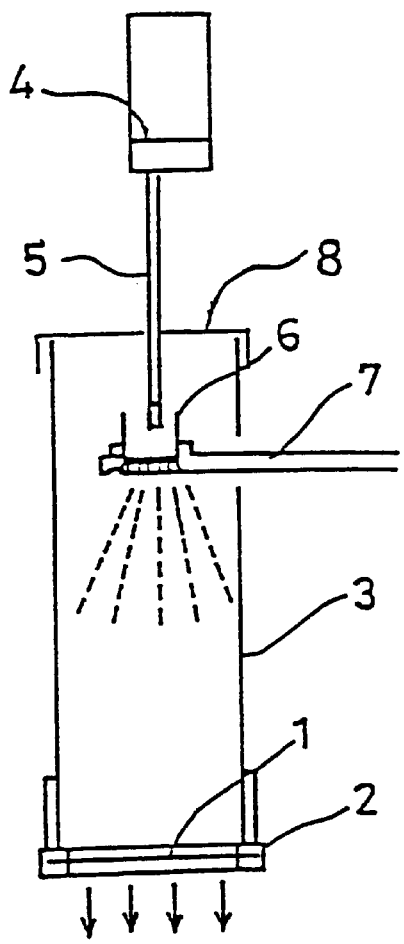
FIG. 1 is a schematic diagram of a spraying apparatus for spraying a sample onto a filter.

FIG. 1 is a schematic diagram of a spraying apparatus for spraying a sample onto a membrane filter.

Figure 2:
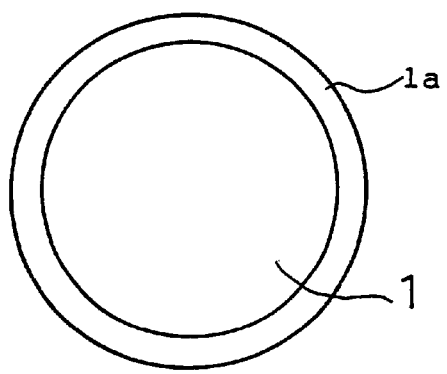
FIG. 2 is a diagram of a membrane filter.

FIG. 2 is a diagram of a filter 1 comprising a polycarbonate film and a ring frame welded thereon. A cylinder 3 is positioned on a top part of the sample base 2 which supports the filter 1. A reagent tank 4 for accommodating the reagent to be delivered to the filter 1 is positioned on top of the cylinder 3. The reagent tank 4 supplies the reagent to a fluid supply unit 6 provided within the cylinder 3 via a drip tube 5 that penetrates the cover of the cylinder 3 and extends to a position approximately 2.0 mm above the fluid supply unit 6. It should be noted that the drip tube 5 is finely positioned and supported so that the dripped reagent always passes through a perforated plate provided on the fluid supply unit 6. The fluid supply unit 6 is supported by an ultrasonic vibrator 7 that vibrates so as to turn the reagent supplied to the fluid supply unit 6 from the reagent tank 4 via the drip tube 5 into a spray state, which spray is then dropped onto the filter 1. It should be noted that the resonance frequency of the vibrator 7 is adjusted to the natural frequency of the vibrator 7 so as to supply with certainty and precision a single reagent spray sample at a time.

The filter sprayed with reagent in the second operation described above is then, in the third operation, presented for example to a bioluminescence image analyzer to determine the plate count. Such an image analyzer can detect even very faint spots of light and, when used in conjunction with the sample preparation apparatus and spray apparatus, can provide fast, simple and reliable plate counts.

Figure 3:
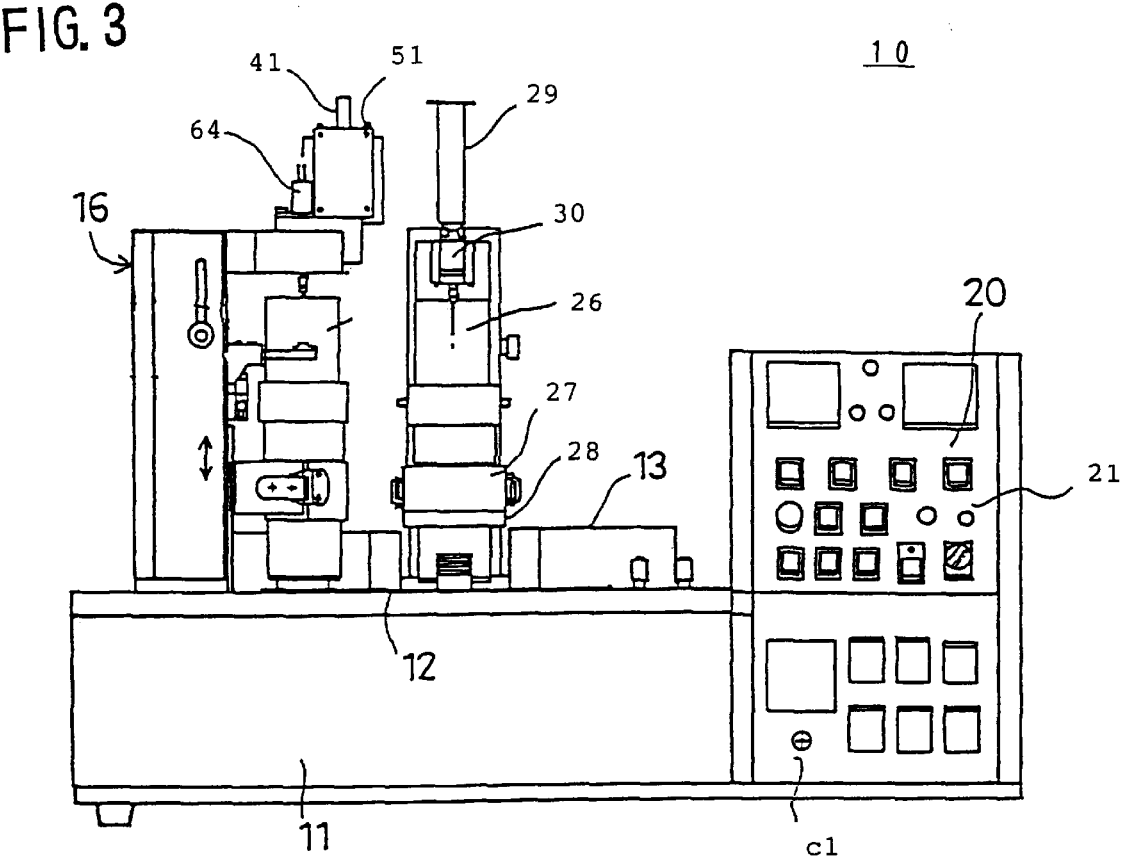
FIG. 3 is a diagram showing a front view of the sample preparation apparatus for preparing a sample for obtaining a plate count using the spraying apparatus according to the present invention.
Figure 4:
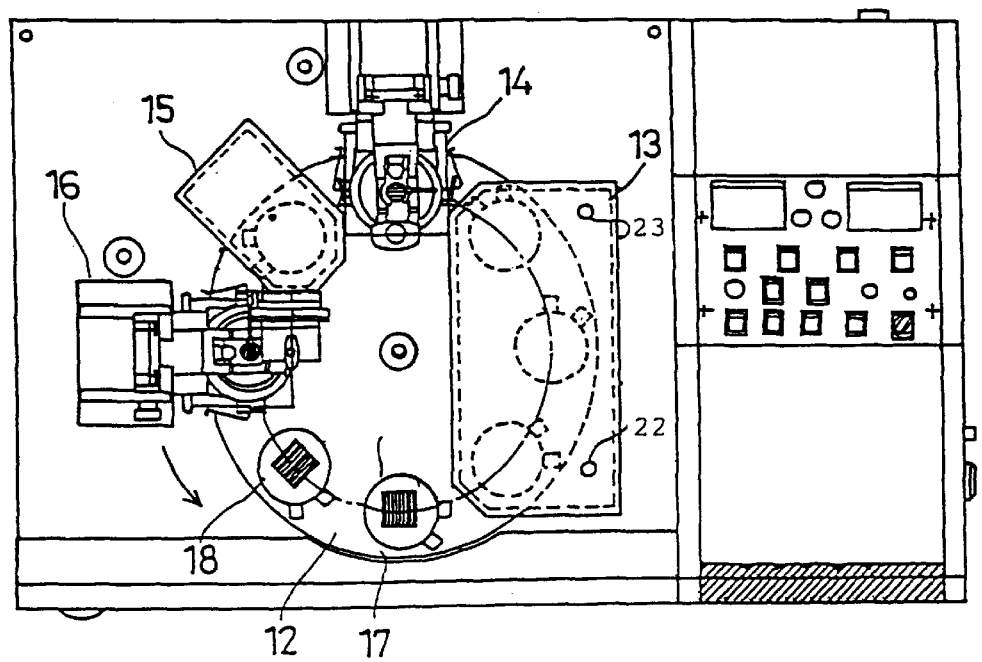
FIG. 4 is a diagram showing a plan view of the sample preparation apparatus.

FIG. 3 and FIG. 4 show the overall construction of a sample preparation apparatus for preparing samples for plate count determination employing the spraying apparatus of the present invention. FIG. 3 depicts a front view of the apparatus and FIG. 4 depicts a plan view of the apparatus. Th sample preparation apparatus 10 comprises a base 11; a turntable 12 provided on the base 11; a first drying chamber 13, an extractant spray apparatus 14, a second drying chamber 15, a luminescent reagent spray apparatus 16, a filter insertion unit 17 and a filter removal unit 18, disposed along a periphery of the turntable 12 in a direction of rotation of the turntable 12. Additionally, the sample preparation apparatus 10 further comprises a control unit 20 having a control panel 21 for controlling the operation of the turntable 12 and the spraying apparatus 14. It should be noted that reference number C1 is a resonance frequency adjustment knob for adjusting the resonance frequency of the vibrator 7 of the reagent spray apparatus.

The first drying chamber 13 is composed of a chamber capable of containing three sample bases 2 and having a heated air intake and an exhaust port 22, such that by the introduction of heated air the chamber is maintained at a predetermined temperature. Additionally, the second drying chamber 15 is composed of a chamber capable of containing one sample base 2. As with the first drying chamber 13, the second drying chamber 15 is similarly maintained at a predetermined temperature by an intake port and exhaust port 23, and dries the filters sprayed with extractant by the extractant spray apparatus 14. Moreover, referring to a drying chamber, it is not always necessary, for example, when a reagent is very volatile.

Figure 5:
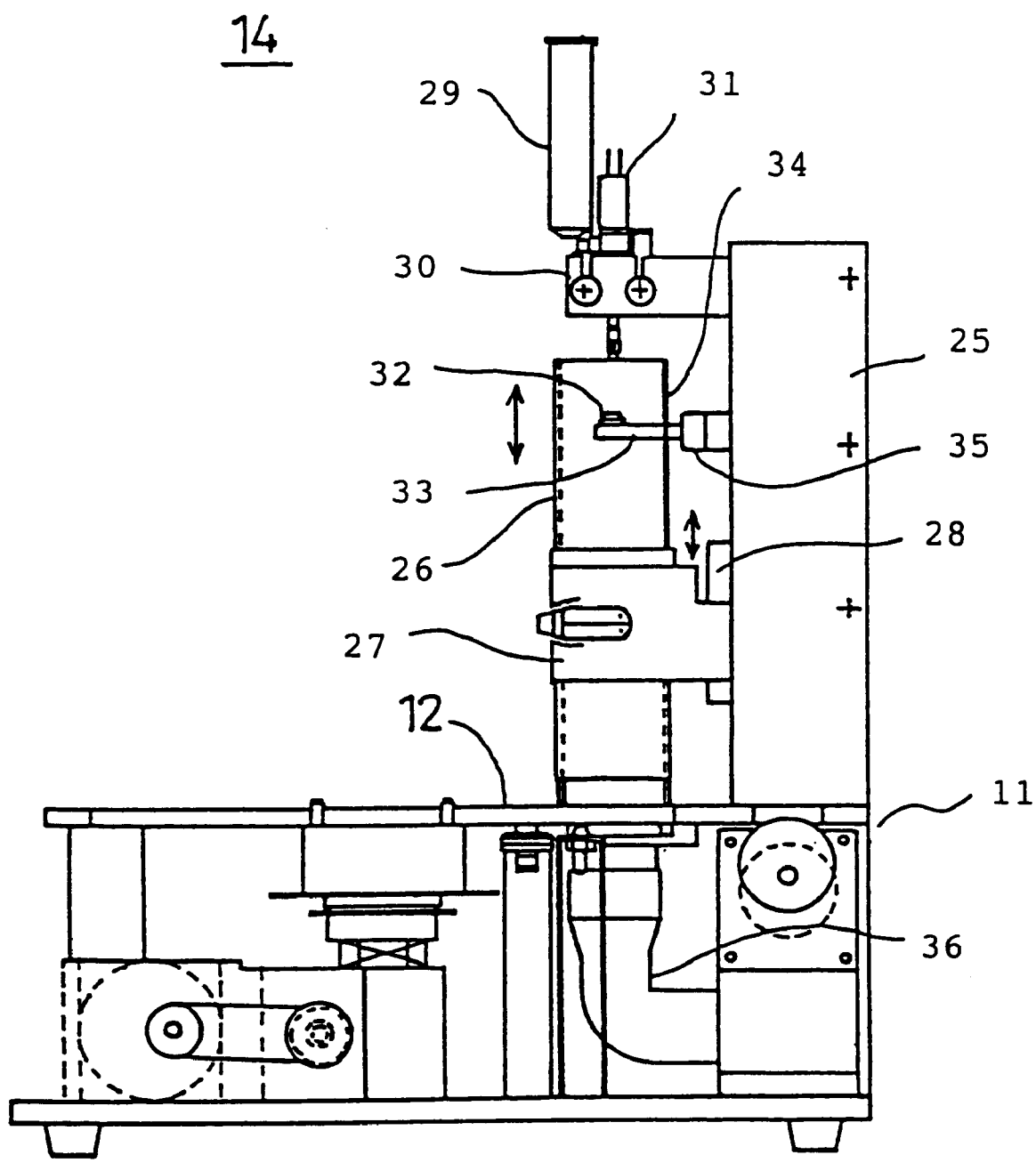
FIG. 5 is a diagram showing a side view of the sample preparation apparatus.

The extractant spray apparatus 14 will be described with reference to FIG. 5, which is a diagram showing a side view of the sample preparation apparatus of the present invention. The extractant spray apparatus 14 has a supporting pillar 25 mounted on a base 11 and equipped with an air cylinder 28 that vertically drives a supporting member 27 that supports a cylinder 26. Additionally, an extractant tank 29 containing an extractant and a flow control unit 30 for controlling the flow of the extractant is positioned at the top of the supporting pillar 25. It should be noted that reference number 31 is a solenoid valve for operating a control valve of the flow control unit 30. Additionally, a supporting assembly 33 for supporting the fluid supply unit 32 positioned within the cylinder 26 is mounted so as to communicate with the ultrasonic vibrator 35 through a slit 34 formed on a side wall of the cylinder 26.

A suction unit 36 is located on the bottom of the turntable 12, so as to withdraw the air inside the cylinder 26 via a filter supported by the turntable 12 support base 2.

It should be noted that the luminescent reagent spray apparatus 16 has essentially the same construction as the extractant spray apparatus 14 described above, so a description of features in common will be omitted. One difference is that the reagent holding tank 41 of the luminescent reagent spray apparatus 16 is equipped with a cooling device 51 whereas the extractant spray apparatus 14 is not. A description of this cooling device 51 will be provided later.

Figure 6:
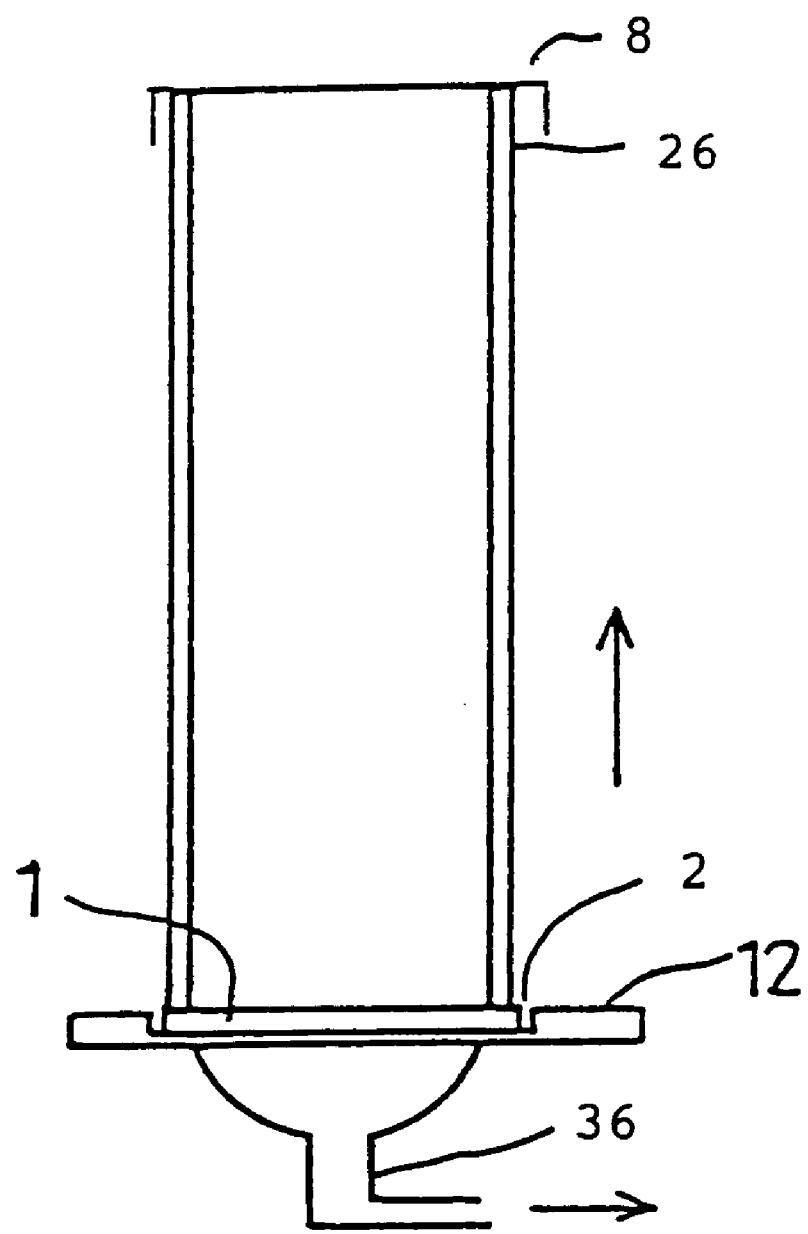
FIG. 6 is a diagram showing a state in which a filter is provided on a turntable sample base.

FIG. 6 is a diagram showing a state in which a filter 1 is provided on a sample base 2 of the turntable 12, and more particularly, a state in which the cylinder has been moved downward so as to spray the filter 1 which has moved into the position of the cylinder 26 of the extractant spray apparatus 14.

The diameter of the cylinder 26 is identical to the diameter of the filter 1. As a result, the filter 1 is sealed by the cylinder 26, in such a way that the reagent spray within the cylinder is not dispersed outside the cylinder. Additionally, the suction unit 36 on the bottom of the sample base 2 withdraws the air from within the cylinder 26.

After spraying has been completed the cylinder 26 moves upward due to the movement of the sample base 2 of the cylinder 26, though at this time trace amounts of reagent may enter the contact surface between the cylinder 26 and the filter 1, sometimes raising the filter 1. In that case the filter 1 may come loose from the sample base 2 and thereby become unavailable for the next operation. In order to prevent such an occurrence it is necessary to secure the filter 1 firmly to the sample base 2 when the cylinder 26 is rising.

The suction unit 36 mounted on the bottom of the sample base 2 is used for the purpose of securing the filter to the sample base 2. By exerting a downward suction the filter 1 can be secured to the sample base 2. It should be noted that the strength of the suction generated by the suction unit 36 may be 5–50 mmHg for 1–5 seconds, preferably 10–30 mmHg for 1–5 seconds.

Figure 7:
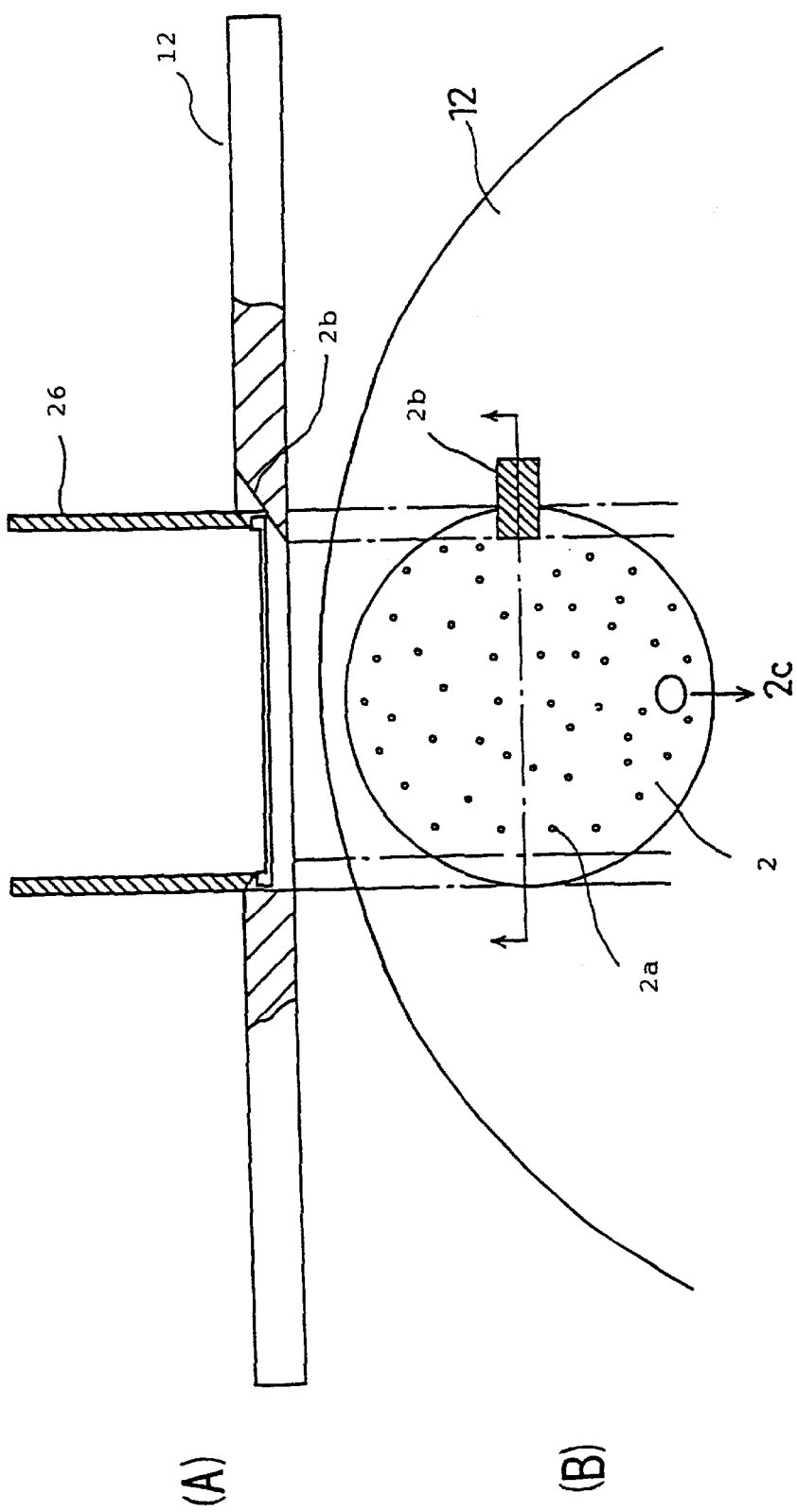
FIG. 7 is a diagram showing an expanded view of the sample base including a front view (A) and a plain view (B).

FIG. 7 is an expanded view of the sample base 2. In order to facilitate understanding this diagram comprises a three-dimensional view to which the cylinder 26 has been added to the plan view. The sample base 2 is recessed into the surface of the turntable 12 to a depth of approximately 1–5 mm, preferably approximately 3 mm. The diameter of the sample base 2 is slightly larger than the diameter of the filter 1, by approximately 0.5 mm. As depicted in the diagram, the sample base 2 shapes the frame 1a of the filter 1 by using a circular concavity formed on the sample base 2. By providing a concavity of a predetermined depth on the sample base 2, a filter 1 mounted on the sample base 2 will lie substantially flat upon the surface of the table, thereby ensuring that the filter 1 will not be knocked off the turntable 12 when the turntable 12 moves.

A plurality of small holes 2a are formed in the floor of the sample base 2 so as to permit the suction unit mounted on the bottom of the turntable 12 to suctionally attach the filter 1 output to the sample base 2.

Additionally, an inclined notch 2b is cut into a portion of the periphery of the turntable from the upper surface of the turntable to the lower surface of the turntable. As will be appreciated from the foregoing description, the handling of the filter 1 is done without any manual intervention. However, the filter 1, once it is fitted to the sample base 2, can be difficult to remove therefrom. This notch 2b is provided in order to ease the removal of the filter 1 from the sample base 2.

Separately, by providing a through-hole aperture 2c in the floor of the sample base 2 it is possible for a light sensor mounted at the bottom of the turntable 12 to determine whether or not a filter 1 is present on the sample base 2.

Figure 8:
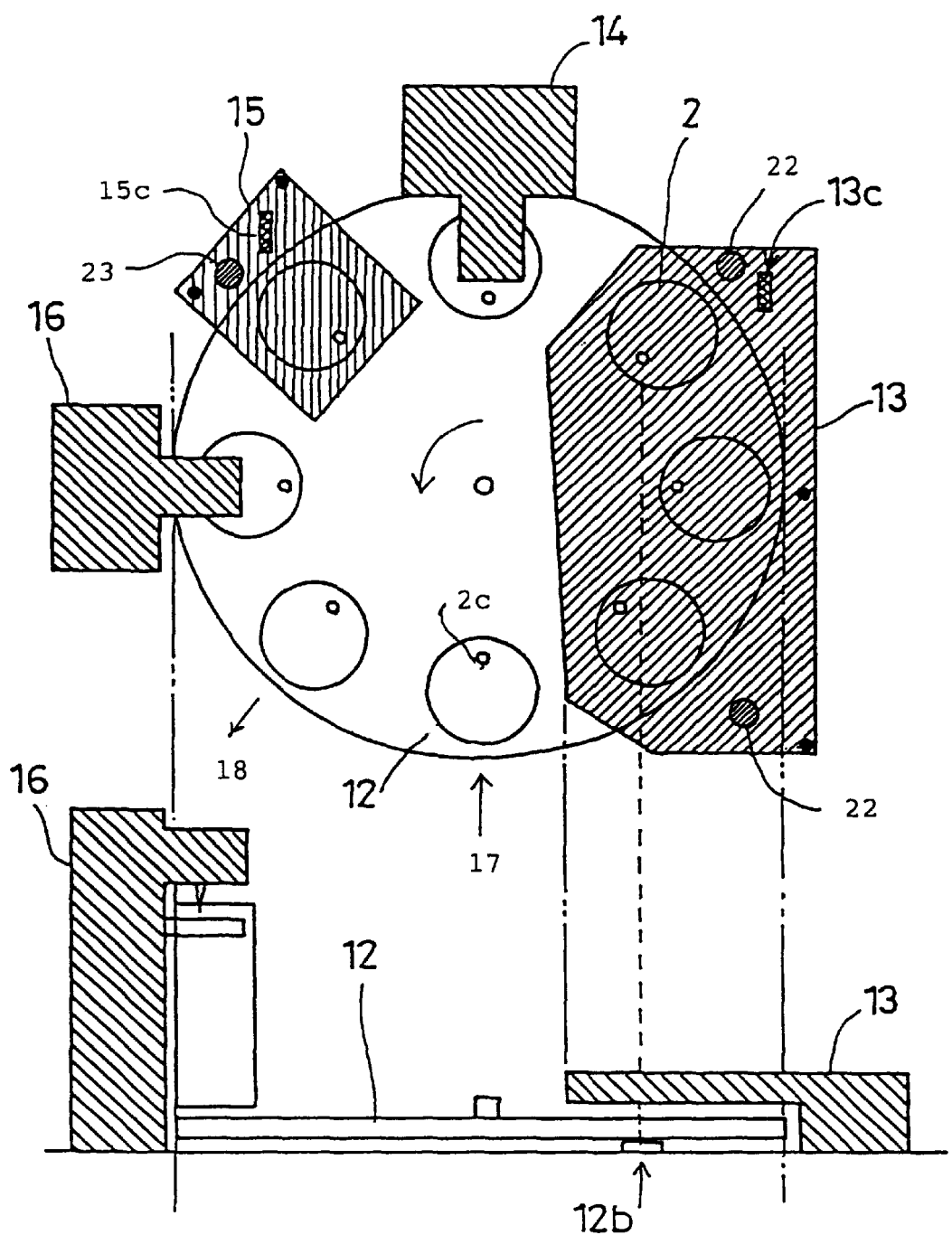
FIG. 8 is a diagram for explaining the individual processing operations to which the filters are subjected as the turntable rotates.

FIG. 8 is a diagram for explaining the individual processing operations to which the filters are subjected as the turntable rotates. As depicted in the diagram the eight sample bases 2 are mounted on the turntable 12. Filters on which microorganisms have been isolated are then placed atop the sample bases 2 by the filter insertion unit 17, the turntable 12 rotated in the counterclockwise direction as shown in FIG. 8 and the filters exposed, in order, to the first drying chamber 13, the extractant spray apparatus 14, the second drying chamber 15 and the luminescent reagent spray apparatus 16, after which the prepared filters are then removed by the filter 1 removal unit 18.

The eight sample bases 2 are arranged so that when one sample base 2 is positioned at the filter insertion unit 17 three sample bases 2 are positioned at the first drying chamber 13, one sample base 2 is positioned at the extractant spray apparatus 14, one sample base 2 is positioned at the second drying chamber 15, one sample base 2 is positioned at the luminescent reagent spray apparatus 16 and one sample base 2 is positioned at the filter 1 removal unit 18. Additionally, eight light sensors 12b for determining whether or not a sample is present on the filter 1 are mounted at the bottom of the turntable 12 in such a way as to correspond to the position of each of the individual processing units, so that a light sensor 12b is positioned at each of the sample bases 2 of the third sample base of the first drying chamber 13, the extractant spray apparatus 14, the second drying chamber 15, the luminescent reagent spray apparatus 16. Additionally, a through-hole aperture 2c is formed in the floor of each of the sample bases 2, such that when the turntable 12 rotates, these through-hole aperture 2c are aligned with the light sensor 12b. The detection beam emitted from the light sensor 12b passes through the through-hole aperture 2c when the sample base 2 is above the light sensor 12b. If there is a filter 1 on the sample base 2 the light sensor 12b will detect it and determine that a filter 1 is present. If there is no filter 1 on the sample base 2 the detection beam will not return and the light sensor 12b will determine that a filter 1 is not present. As will be explained later, this information regarding the presence or absence of a filter 1 on the sample base 2 will be used in the control of the luminescent reagent spray apparatus 16 and the operation of the turntable 12.

As described earlier, the first drying chamber 13 is composed of a chamber capable of containing three sample bases 2 and having a heated air intake and an exhaust port 22, such that by the introduction of heated air the chamber is maintained at a predetermined temperature by a temperature sensor 13c. Additionally, the second drying chamber 15 is composed of a chamber capable of containing one sample base 2. As with the first drying chamber 13, the second drying chamber 15 is similarly maintained at a predetermined temperature and equipped with an intake port and an exhaust port 23 and dries the filters sprayed with extractant by the extractant spray apparatus 14.

Figure 9:
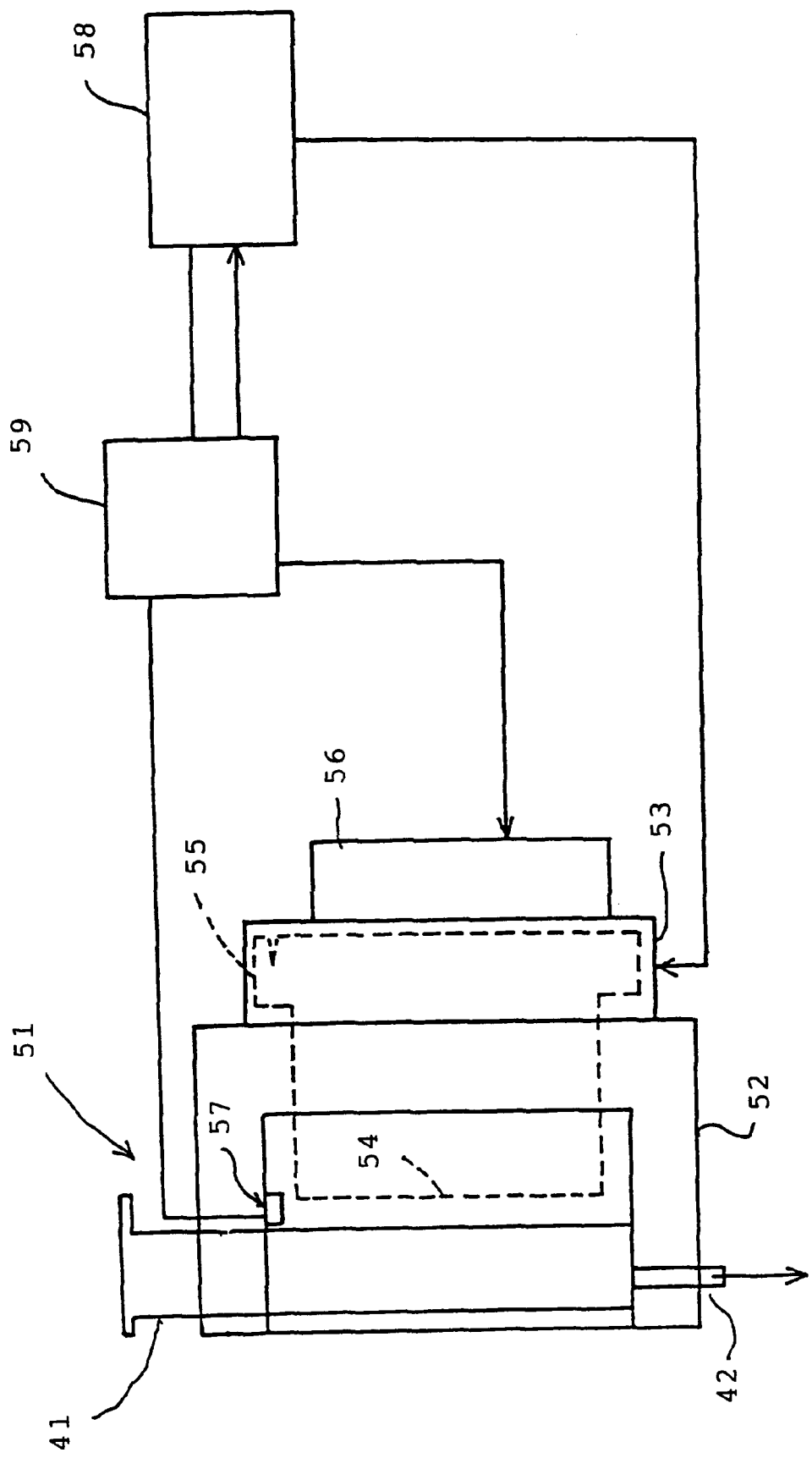
FIG. 9 is a diagram of a cooling device for a luminescent reagent holding tank for a luminescent reagent spray apparatus.

A description will now be given of the reagent supply unit of the luminescent reagent spray apparatus 16 by reference to FIG. 9, FIG. 10 and FIG. 11.

As noted earlier, the reagent holding tank 41 of the luminescent reagent spray apparatus 16 is provided with a cooling device 51. The cooling device 51, as shown in FIG. 8 and again in FIG. 9, comprises a cooling chamber 52 itself composed of insulating material enclosing the reagent holding tank 41. Further, the cooling device 51 also comprises a cooling unit 53 for cooling the cooling chamber 52. The cooling unit 53 utilizes the Peltier effect generated by a heat collector 54 inside the cooling chamber 52 and a radiator 55 outside the cooling chamber 52, and so a cooling fan 56 is mounted on the radiator 55. The cooling device 51 is provided with a temperature sensor 57 mounted inside the cooling chamber 52 for sensing the temperature inside the cooling chamber 52, a cooling unit driver 58 for driving a cooling unit based on values measured by the temperature sensor 57, and a control unit 59 for controlling the cooling fan 56. The temperature inside the cooling chamber should be 2–15° C., and preferably 4° C.

As shown in FIG. 10, at least a portion of the cooling chamber 52 is composed of a window 52a made of a transparent material such as, for example, polycarbonate, such that the inside of the reagent holding tank 41 can be observed. Part or all of the reagent holding tank 41 may be made of a transparent material, or, alternately, a means for indicating the amount of reagent remaining in the tank may be provided, such that it is possible to know how much reagent remains by looking through the window 52a of the cooling chamber 52 from the outside thereof.

FIG. 11 is a diagram of a flow control unit 60 connected to the luminescent reagent holding tank 41. The flow control unit 60 comprises a support block 61 supporting a solenoid valve 64, a connecting passage 62 in which is inserted a connecting tube 42 mounted at the bottom of the luminescent reagent holding tank 41, and a drip nozzle 63 for dripping reagent onto a fluid supply unit supported from below by a vibrator via the solenoid valve 64 from the connecting passage 62. Accordingly, the connecting tube 42 at the bottom of the luminescent reagent holding tank 41 of FIG. 10 is inserted into the connecting passage 62 of the flow control unit 60, by which both are integrated into a single assembly.

As shown in the expanded diagram in FIG. 11, the valve mechanism of the solenoid valve 64 comprises a tube 65 and shaft 66. Reagent supplied via a flow inlet 67 communicating with a connecting passage 62 is supplied by electromagnetic induction to the fluid supply unit via the drip nozzle 63 from a gap between a valve tip portion 68 and a valve seat 69 in conjunction with the vertical movement of the shaft 66.

It should be noted that the structure of the flow control unit 60 of the luminescent reagent spray apparatus 16 as described in FIG. 11 is identical to that of the flow control unit 30 of the extractant spray apparatus 14.

Figure 12:
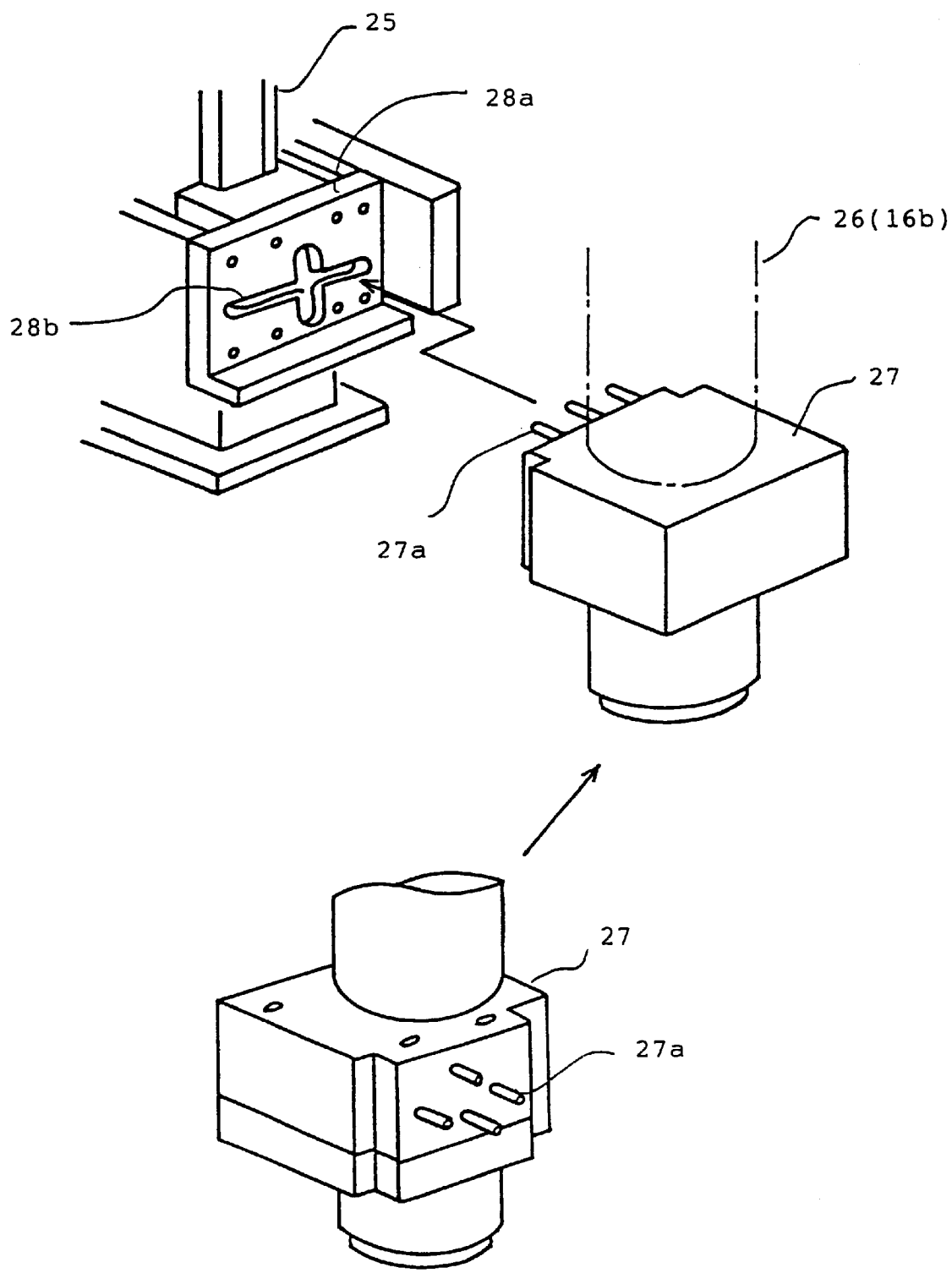
FIG. 12 is a diagram of a mounting assembly for mounting a cylinder.

FIG. 12 is a diagram of a mounting assembly for mounting a cylinder 26 on the supporting pillar 25 of the extractant spray apparatus 14. The air cylinder 28 mounted on the supporting pillar 25 has a mounting part 28a, on which is formed a cross-shaped fitting groove 28b. At the same time, the cylinder support member 27 has four pins 27a arranged in the shape of a cross so as to fit into the fitting groove 28b formed on the mounting part 28a. By fitting the pins 27a of the cylinder support member 27 into the fitting groove 28b formed on the mounting part 28a of the air cylinder 28 the cylinder 26 can be freely attached to and detached from the supporting pillar 25.

It should be noted that the cylinder mounting assembly of the luminescent reagent spray apparatus 16 has a structure that is identical to that of the extractant spray apparatus 14, so a description thereof is omitted.

FIG. 13 is a diagram of a sensor unit for detecting a spray state and its mounting assembly, the sensor unit to be mounted on the extractant spray apparatus cylinder 26 and on the luminescent reagent spray apparatus cylinder 16b. A description will be given of the sensor unit using the extractant spray apparatus cylinder 26 as an example.

The sensor unit 70 comprises a cylindrical member 71 that is fitted over the exterior of the cylinder 26. A through-hole aperture 73 into which is inserted the light sensor 72 is formed on the cylindrical member 71, as is a screw hole 75 into which a stopper 74 is screwed so as to affix the cylindrical member 71 to the outer periphery of the cylinder 26. A reflective panel 76 is mounted on an inner surface of the cylindrical member 71. This reflective panel 76 reflects the light emitted from the light sensor 72 back to the light sensor 72. As shown in FIG. 13, the stopper 74 comprises a screw portion 74a and a tip ball bearing portion 74b, the ball bearing positioned so as to be able to freely advanced and withdrawn by a spring 74c.

At the same time, the cylinder 26 mounting the sensor unit 70 is itself composed of a transparent glass or plastic material, on a wall of which are formed a through-hole aperture 77 into which the light sensor 72 is inserted and a stop hole 78 into which the stopper tip ball bearing 74b is fitted. The through-hole aperture 77 and the stop hole 78 are arranged with respect to each other so as to correspond to the arrangement of the through-hole aperture 73 and screw hole 75 formed on the cylindrical member 71 of the sensor unit 70.

A description will now be given of a mounting on the cylinder 26 of the sensor unit 70 constructed as described.

The screw portion 74a of the stopper 74 is screwed into the screw hole 75 of the cylindrical member 71 of the sensor unit 70. It should be noted that the stopper 74 is designed so that only the tip ball bearing portion 74b protrudes beyond the inner wall surface of the cylindrical member 71 when the stopper is mounted on the cylindrical member 71. Next, the cylindrical member 71 mounting the stopper 74 is inserted over the cylinder 26. In such a state the tip ball bearing portion 74b is pushed inward so as to permit the cylindrical member 71 to slide across the outer surface of the cylinder 26. The cylindrical member 71 is then slidably rotated in such a way that the tip ball bearing 74b of the stopper 74 is positioned at the stop hole 78 formed in the wall of the cylinder 26, at which point the ball bearing 74b is impelled outward by the spring 74c so as to enter and engage the stop hole 78, thereby attaching the cylindrical member 71 to the outer wall of the cylinder 26. At this time the through-hole aperture 73 on the cylindrical portion 71 for mounting the sensor unit 70 and the through-hole aperture 77 on the cylinder 26 are in a concentric state. The tip of the light sensor 72 is then inserted into and through the through-hole aperture 72 and the through-hole aperture 77 so as to be positioned inside the cylinder 26. Thus the light sensor 72 and the sensor unit 70 having the reflective panel can be attached to the cylinder 26.

A description will now be given of the detection of the spray state inside the cylinder 26 by means of the sensor unit 70 mounted on the outer periphery of the cylinder 26.

The light emitted from the light sensor 72 is reflected by the reflective panel 76 back to the light sensor. At this time the level of light received by the light sensor 72 varies according to the state of the reagent spray inside the cylinder 26. Accordingly, by measuring the change in light level and time it is possible to determine whether or not an optimum spray state has been obtained. Accordingly, the output signal of this light sensor 72 can, for example, be used to detect spray condition of an automated spray apparatus.

It should be noted that although the sensor unit 70 mounting assembly in the example described above is mounted on the extractant spray apparatus cylinder 26, an identical structure can be mounted on the luminescent reagent spray apparatus cylinder 26.

As described above, the spray apparatus of the present embodiment has a structure that provides a cylinder 26 provided with a reagent spraying means that is movable with respect to a sample base 2 itself movable by means of a turntable, such that a filter moved by means of the turntable can be sprayed with reagent, a plurality of such filters can be sprayed with reagent quickly and an apparatus can be automated. Additionally, the cylinder 26 that comprises the spraying apparatus is detachably attached to the drive unit thereof, so that cleaning, inspection and maintenance can be performed with ease. Additionally, the reagent holding tank and drip nozzle can be separated to permit easy inspection and maintenance of the drip nozzle.

Additionally, as described above the sample base 2 formed on the turntable is formed by a circular concavity formed to a predetermined depth and an inclined notch is cut into a portion of the periphery of the turntable from an upper surface of the turntable to a lower surface of the turntable. As a result, the filter can be securely supported and, at the same time, can be removed with ease.

A description will now be given of the operation of the above-described sample preparation apparatus 10 and the operations performed by the control unit.

Figure 14:
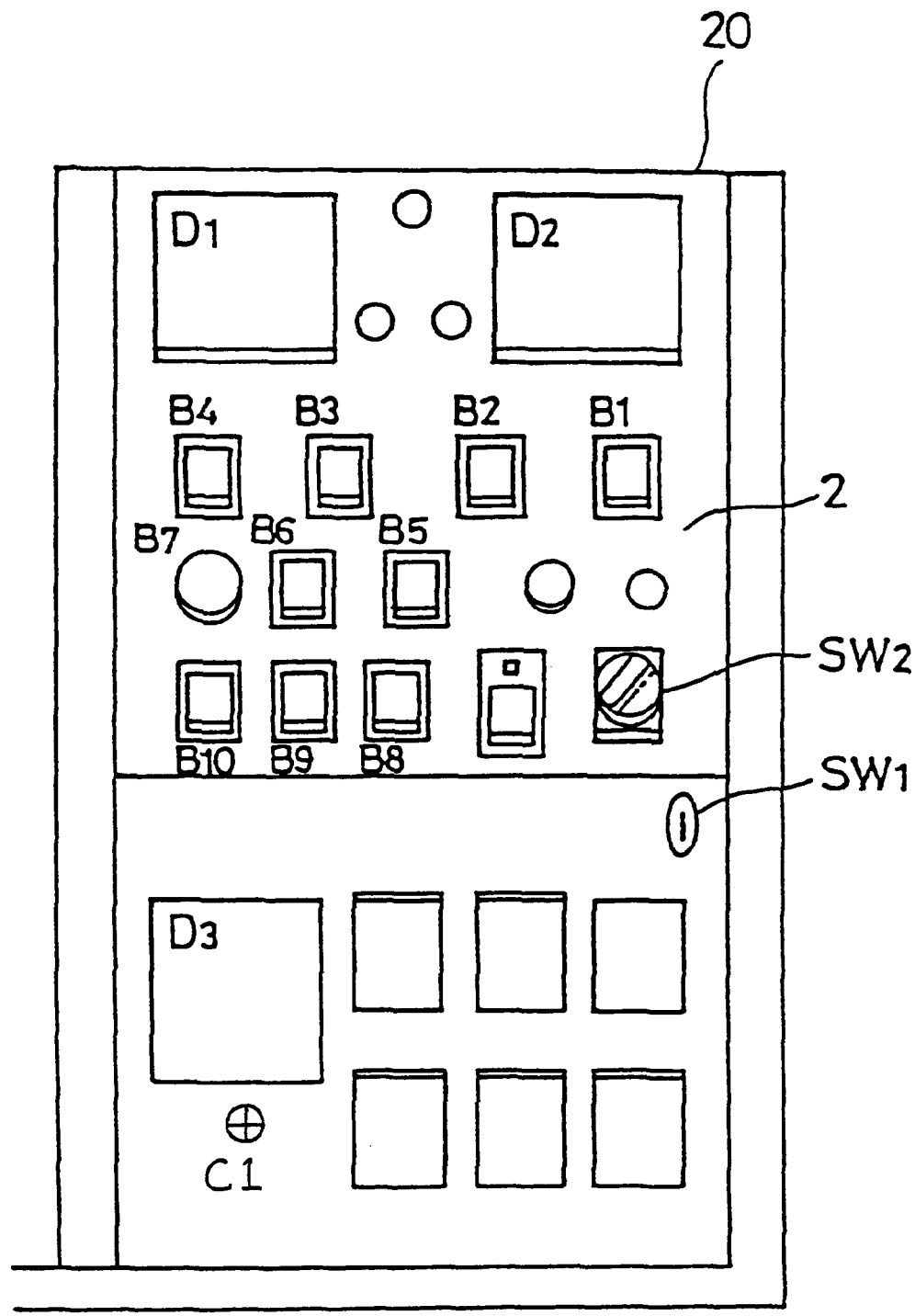
FIG. 14 is a diagram of the arrangement of controls on a control panel of a control unit.

FIG. 14 is a diagram of the arrangement of controls on a control panel 21 of a control unit 20 for controlling the various operations of the sample preparation apparatus 10 depicted in FIG. 3. D1, D2 and D3 are display devices, with D1 being a temperature display for the cooling unit 21, D2 a temperature display for the first and second drying chambers 13, 15, and D3 a display for a setting of a standby time. B1–B10 are various control buttons, with B1 being a button for manually operating the extractant spray apparatus drip 14, B2 a button for activating the ultrasonic vibrator and thereby performing spraying, B3 a button for manually operating the luminescent reagent spray apparatus 16 reagent drip, B4 a button for spraying luminescent reagent, B5 a cylinder drive button for manually driving the cylinder 26 that moves the extractant spray apparatus 14 cylinder 14b up and down, B6 a cylinder drive button for manually driving the cylinder 16b that moves the luminescent reagent spray apparatus 16 up and down, B7 a stop button, B8 a turntable operating button for rotatably driving the turntable 12, B9 a button for moving the extractant spray apparatus 14 up and down, dripping and then spraying the extractant, and B10 a button for moving the extractant spray apparatus 14 up and down, dripping and then spraying the reagent. Additionally, C1 is a resonance frequency adjustment knob for adjusting the amount of reagent sprayed. Additionally, SW1 is a power switch and SW2 is a sample preparation apparatus operating mode switch for selectively switching between manual and automatic operating modes.

A description will now be given of steps in the production of a sample to be used with a plate count measuring apparatus using the sample preparation apparatus of the present embodiment as described above, with reference to FIG. 15, FIG. 16, FIG. 17 and FIG. 18.

The sample preparation apparatus 10 is configured so as to permit selective switching between a manual mode for performing all operations manually and an automatic mode for performing predetermined operations automatically. The operation of preparing a sample using the sample preparation apparatus 10 does involve manually setting the filter 1 on the sample base 2 as well as manually removing the processed filter 1. However, all other operations are automated.

Figure 15:
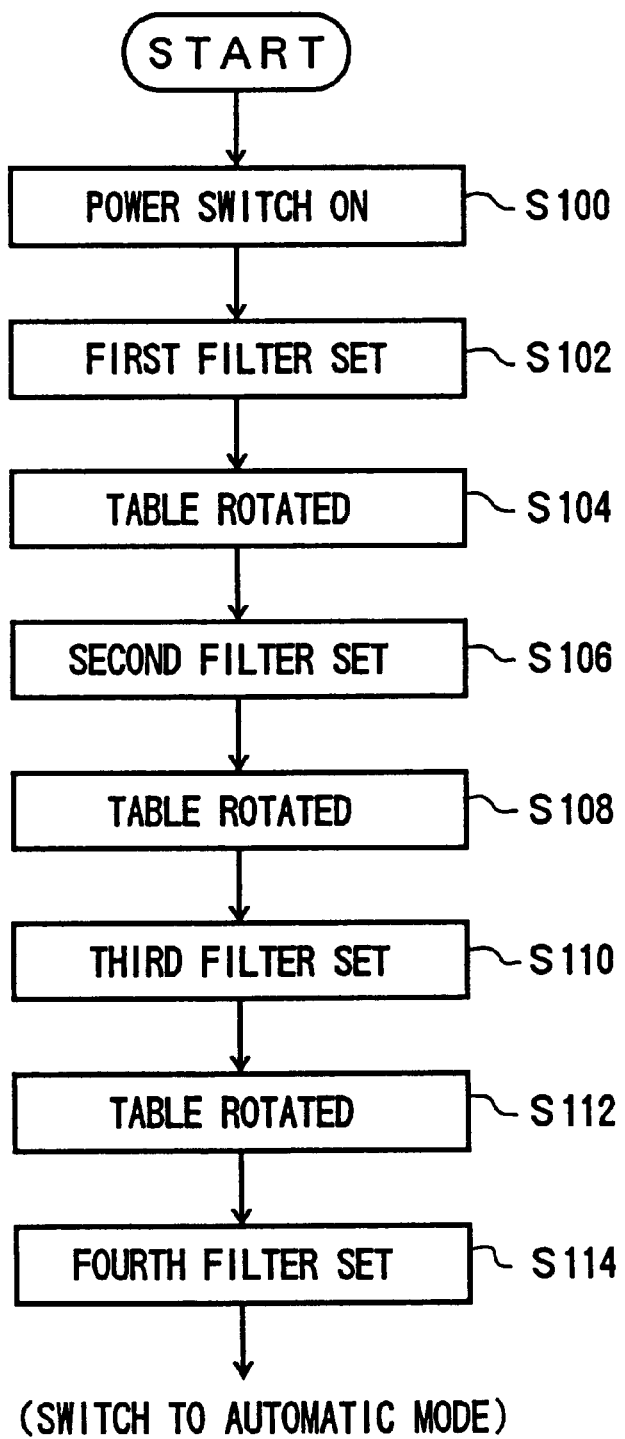
FIG. 15 is a flow chart showing steps in the operation of a manual mode of the sample preparation apparatus.
Figure 16:
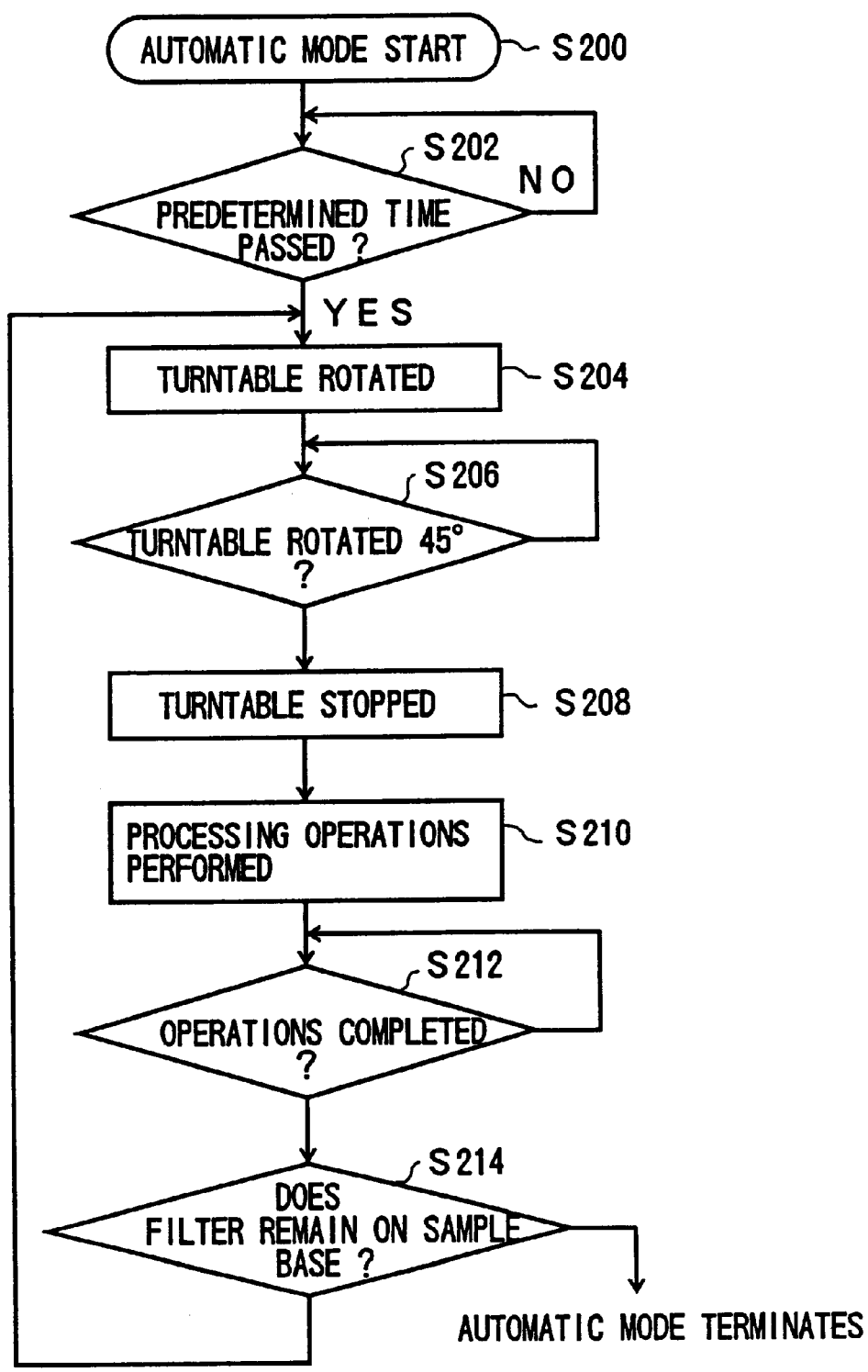
FIG. 16 is a flow chart showing steps in the operation of an automatic mode of the sample preparation apparatus.

FIG. 15 is a flow chart showing steps in the operation of a manual mode of the sample preparation apparatus. As shown in FIG. 15, in an initial step S100 the power switch SW1 is turned ON and the operating mode switch SW2 is set to manual. When the power switch SW1 is turned ON the first drying chamber 13 and the second drying chamber 15 are activated and heated air of a predetermined temperature is introduced therein.

With the sample preparation apparatus 10 in the state described above the operator sets the first filter 1 onto the sample base 2 from the turntable filter 1 insertion unit 17 in a step S102. By pressing the turntable operating button B8 the turntable is rotated in a step S104. By so doing the turntable rotates through an arc of 45° and then stops. Accordingly, the first filter 1 set upon the sample base 2 is moved to the first drying chamber 13 and the next sample base 2 is positioned at the filter 1 insertion unit 17. The second filter 1 is then set on the sample base 2 and the turntable operating button B8 is pressed again, in steps S106 and S108. As a result, three filters are set upon respective sample bases and the turntable rotated so that the three filters are contained in the first drying chamber 13 in steps S110 and S112. At this time a fourth filter 1 is set on a sample base 12a from the filter 1 insertion unit 17 in a step S114. These operations are performed manually.

With the sample preparation apparatus 10 in a state in which the fourth filter 1 is set on the sample base 12a the operating mode switch SW2 is set to the automatic mode. By switching to the automatic mode the control unit 20 automatically performs the sequence of operations depicted in the flow chart shown in FIG. 16.

By switching to the automatic mode the automatic mode is started in a step S200. In so doing, a timer on the sample preparation apparatus 10 starts a clock running and maintains a standby status until a predetermined time has elapsed in a step S202. This standby time is set as to satisfy conditions for drying by the first drying chamber 13 and the second drying chamber 15, and in this example is set at 2 minutes. After a predetermined time period as elapsed the turntable 12 is rotated 45° in a step S204. The turntable 12 is equipped with a rotation detection sensor to detect the angle of rotation in a step S206, such that the control unit stops the rotation when the sensor detects a 45° rotation. As a result, the first filter 1 in the first drying chamber 13 is moved to the extractant spray apparatus 14 and the fourth filter 1 is then introduced into the first drying chamber 13.

Next, in a step S210, the relevant operations are performed at the extractant spray apparatus 14 and luminescent reagent spray apparatus 16, as well as at the first drying chamber 13 and the second drying chamber 15. After it is ascertained in a step S212 that these operations have been completed it is then determined in a step S214 whether or not a filter 1 is present on the sample base 2 on the turntable 12. If the presence of a filter 1 is detected then the turntable 12 is once again rotated as in step S204 and the same operations are repeated. If no filter 1 is detected then the automatic mode terminates.

Figure 17:
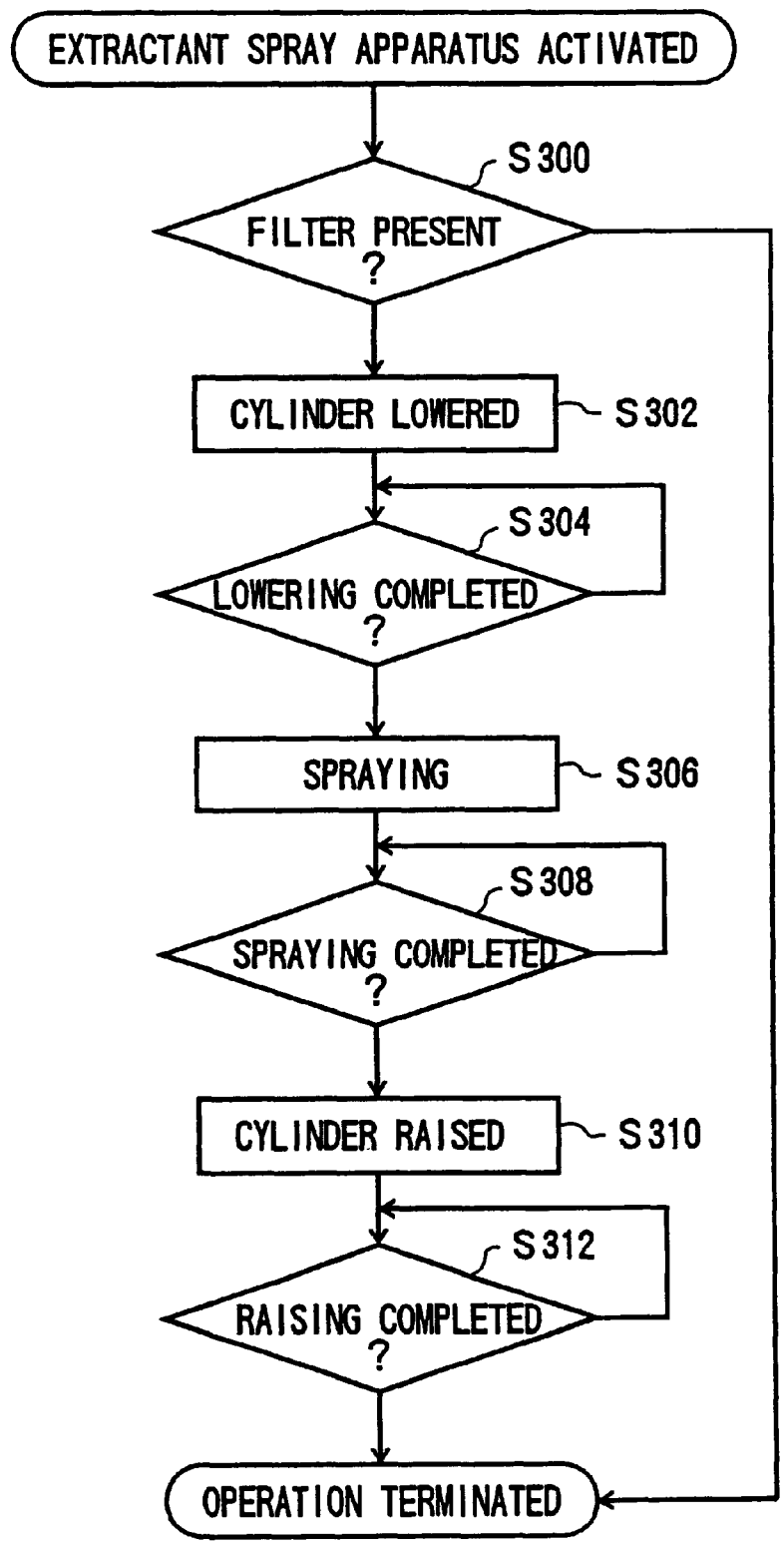
FIG. 17 is a flow chart of operations performed by an extractant spray apparatus.

FIG. 17 is a flow chart of operations performed by an extractant spray apparatus. As noted earlier, sensors for detecting the presence or absence of a filter 1 on the sample base 2 are arranged at positions corresponding to the sample bases 2 of the first drying chamber 13, the extractant spray apparatus 14, the second drying chamber 15 and the luminescent reagent spray apparatus 16 on the bottom the turntable 12. When the rotation of the turntable 12 terminates the control unit 20 determines whether or not filters are present on the sample bases 2 at each of the various processing units described above and, based on the results of that detection, controls in parallel the succeeding operation of these processing units.

Initially, at the position of the extractant spray apparatus 14 the presence or absence of a filter 1 is determined in a step S300. If a filter 1 is detected then the cylinder 26 of the extractant spray apparatus 14 is lowered so as to rest upon a sample base 2 in a step S302. It should be noted that, if no filter 1 is present on the corresponding sample base 2, then this sub-routine terminates. When it is determined by a sensor not shown in the diagram that the cylinder 26 is resting on the sample base 2 in a step S304, then the extractant fluid control unit 30 and the ultrasonic vibrator 35 are activated and spraying of the extractant is performed in a step S306. Then, in a step S308, a sensor unit 70 mounted on the cylinder 26 for detecting the state of spray within the cylinder 26 detects the state of the spray therein. After it has been determined in a step S310 that spraying has been carried out, the cylinder 26 is raised and, after it is determined in a step S312 that the rise of the cylinder 26 has terminated, this sub-routine terminates as well.

The operations performed by the luminescent reagent spray apparatus 16 are essentially the same as those performed by the extractant spray apparatus 14 with the exception that a luminescent reagent is sprayed by the luminescent reagent spray apparatus 16 instead of an extractant sprayed by the extractant spray apparatus 14, and so for convenience these operations shown in the flow chart in FIG. 17 can be re-labeled as steps S400–S412 as appropriate.

Figure 18:
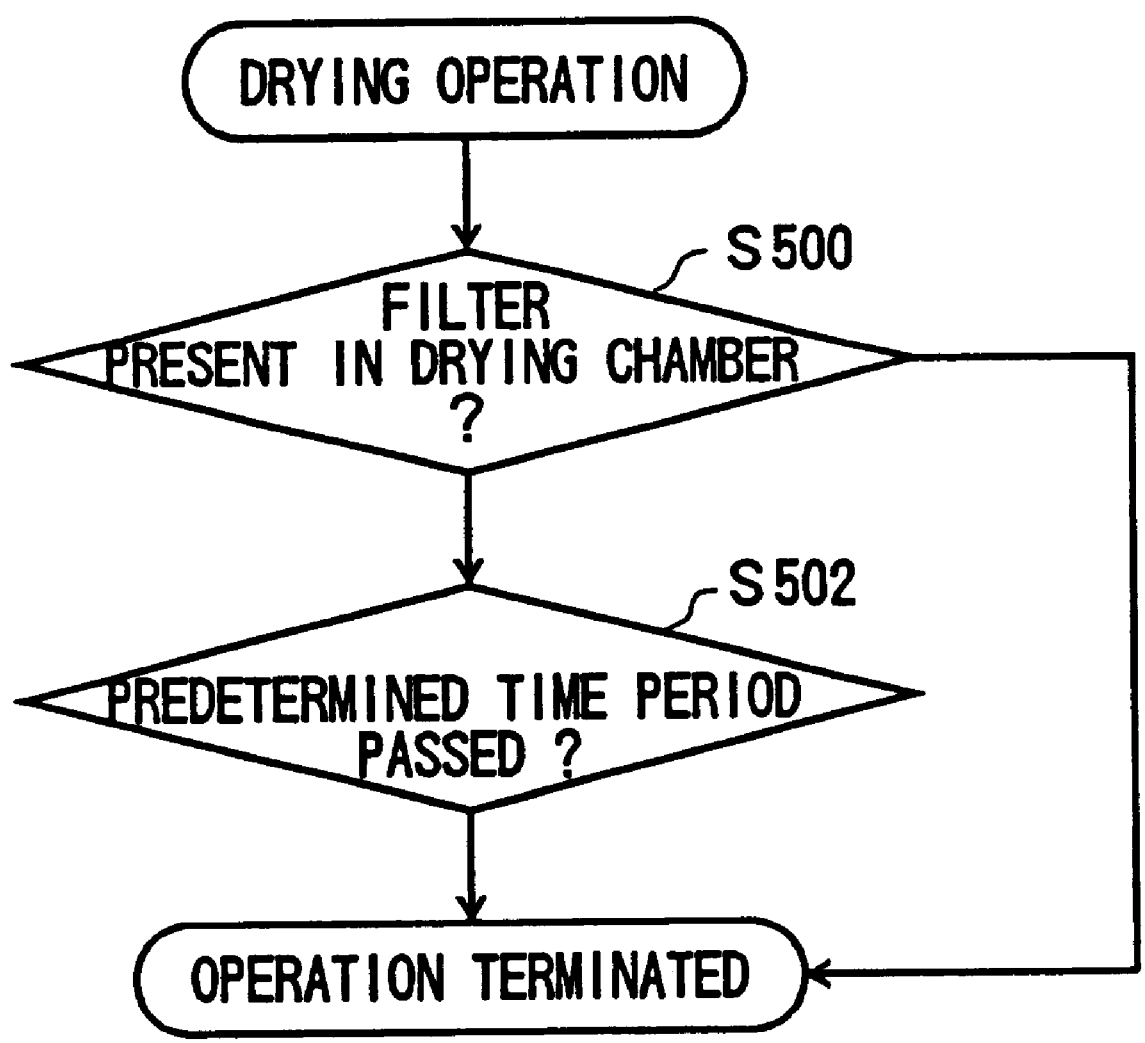
FIG. 18 is a flow chart showing steps in the operation of the drying chambers.

FIG. 18 is a flow chart showing steps in the operation of the drying chambers. In the first drying chamber 13 and the second drying chamber 15 it is first determined in a step S500 whether or not a filter 1 is present on the sample base 2 at a predetermined position. It should be noted that in the present example three such sample bases 2 will be present within the first drying chamber when the turntable 12 ceases to rotate, and in that event it is determined whether or not a filter 1 is present on the third sample base 2. When a filter 1 is present within the drying chamber it is then determined, in a step S502, whether or not a predetermined period of time for drying the filter 1 has elapsed. Once it is determined that such a predetermined period of time has elapsed this sub-routine terminates. This sub-routine also terminates in the event that no filter 1 is present.

As described above, in the automatic operating mode the various operations to be performed are carried out automatically when a filter 1 is present on the sample base 2 on the turntable 12, with the operations performed in succession with each rotation of the turntable 12 on which the sample bases 2 are set.

It should be noted, however, that in the present embodiment of the sample preparation apparatus 10 the work of placing the filter 1 on the sample base 2 and removing the sample once spraying of the reagent has been completed is done manually.

Additionally, it should be noted that although in the above-described example the first three filters were set on corresponding sample bases 2 and then the sample preparation apparatus 10 switched to the automatic operating mode, it is also possible to set the sample preparation apparatus 10 to the automatic operating mode from the beginning. In that case, after the filter 1 has been inserted from the filter 1 insertion unit 17 the operations depicted in the flow chart shown in FIG. 15 are then performed, with step S402 being performed at the time the first filter 1 reaches the third position of the first drying chamber 13.

Additionally, although in the above-described example the drying time for the first drying chamber 13 and the second drying chamber 14 was set at 2 minutes, typically the drying time can range from 1–20 minutes, with a range of between 1 minute 30 seconds and 2 minutes being preferable. Moreover, although the turntable 12 rotation is based on the drying time, the processing time at the extractant spray apparatus 14 and the luminescent reagent spray apparatus 16 is not affected by the time require to raise and lower the cylinder 26 and spray the extractant or reagent because this required time does not exceed 1 minute. Additionally, it should be noted that the drying temperature range is 25° C. to 45° C., preferably 35° C.

Further, the sample preparation apparatus of the present invention can be operated completely manually as well. In that case, the various controls on the control panel 20a of the control unit 20 are operated in order to perform such operations as turntable 12 drive, the raising and lowering of the cylinders of the respective spray apparatuses, the spraying of the extractant and reagent, and so on.

As can be appreciated from the above description, the sample preparation apparatus of the present invention provides quick and easy microorganism counts without the need to move the filters between processing operations and without the need for specialized skill in the operation of the spraying apparatuses.

In the above mentioned embodiment, a filter insertion unit, an extractant spray apparatus, a luminescent reagent spray apparatus and a filter removal unit are disposed in order along a periphery of the turntable on which a plurality of sample bases are formed in a direction of rotation of the turntable. It is, however, possible to substitute the turn table for a conveyer transfer system which is supported by a pair of horizontal axes to move linearly, and to dispose sample bases on a conveyer and a filter insertion unit, an extractant spray apparatus, a luminescent reagent spray apparatus and a filter removal unit in order along the conveyer.

The above description is provided in order to enable any person skilled in the art to make and use the invention and sets forth the best mode contemplated by the inventor of carrying out his invention. The present invention is not limited to the specifically disclosed embodiments and variations, and modifications may be made without departing from the scope of the present invention.

The present application is based on Japanese priority application nos. 10-194608 and 10-194609, both filed on Jul. 9, 1998, the entire contents of each of which are hereby incorporated by reference.

What is claimed is:

1. A sample preparation apparatus for preparing a sample to be used for inspecting a specimen isolated on a filter, comprising:
   a turntable on which a plurality of sample bases are formed;
   a filter insertion unit, a first drying chamber, an ATP extractant spraying apparatus, a second drying chamber, a luminescent reagent spray apparatus and a filter removal unit, disposed in order along a periphery of the turntable in a direction of rotation of the turntable;
   a plurality of sensors configured to detect a filter on one of the sample bases at least prior to spraying of one of the extractant spray apparatus and the luminescent reagent apparatus with respect to the filter; and
   a control unit configured to control respective operations of the turntable, the first drying unit, the extractant spraying apparatus, the second drying unit and the luminescent reagent spray apparatus in response to a result of the detection of each sensor and operational information of the turntable, the first drying unit, the extractant spraying apparatus, the second drying unit and the luminescent reagent spray apparatus.

2. The sample preparation apparatus as claimed in claim 1, wherein:
   the luminescent reagent spray apparatus is supported above the sample base so as to be movable in a vertical direction and comprises a cylinder mountable above the sample base and spray means for spraying a luminescent reagent onto a filter disposed within the cylinder mounted on the sample base.

3. The sample preparation apparatus as claimed in claim 2, wherein the cylinder is positioned above the turntable, supported on a drive unit so as to be movable in a vertical direction, and is freely detachably attached to the drive unit via a mounting assembly.

4. The sample preparation apparatus as claimed in claim 2, further comprising a reagent supply unit for supplying reagent to the cylinder, the reagent supply unit mounted on top of the cylinder; a fluid supply unit supported on a vibrating means and mounted within the cylinder; and a suction unit mounted on the bottom of the sample base, wherein the reagent supply unit has a tank for holding the reagent and a control unit for controlling the amount of reagent to be supplied, the tank and the control unit being detachably connected to each other.

5. The sample preparation apparatus as claimed in claim 2, further comprising a reagent supply unit for supplying reagent to the cylinder, the reagent supply unit mounted on top of the cylinder; a fluid supply unit supported on a vibrating means and mounted within the cylinder; and a suction unit mounted on the bottom of the sample base, wherein the reagent supply unit is accommodated within a cooling chamber having a transparent window.

6. The sample preparation apparatus as claimed in claim 1, wherein the turntable includes a rotation detection sensor configured to detect a rotation of the turntable by a predetermined angle such that the control unit stops the rotation of the turntable when the rotation detection sensor detects the predetermined angle of rotation by the turntable.

7. A sample filter preparation apparatus for preparing plural sample filters to be inspected for a specimen isolated on each of the plural sample filters, comprising:

a turntable having a plurality of sample filter holding means each for holding a sample filter;

filter insertion means for inserting the sample filter onto one of the plurality of sample filter holding means;

first drying mean for drying at least one sample filter;

ATP extractant spraying means for spraying an ATP extractant onto the sample filter;

a second drying means for drying the sample filter;

reagent spray means for spraying a reagent onto the sample filter;

filter removal means for removing the sample filter from the one of the plurality of sample filter holding means;

sensing means for detecting the sample filters on the plurality of sample filter holding means; and control means for controlling at least the ATP etractant spraying means and the reagent spray means to spray the ATP extractant and reagent onto the sample filter when the sample filter is detected.

8. The sample preparation apparatus as claimed in claim 7, wherein the ATP extractant spray means and reagent spray means are provided above the turntable and each comprise a cylinder mountable onto a respective one of the plurality of sample filter holding means for spraying and a spray device configured to spray the ATP extractant and reagent onto the sample filter when the sample filter is positioned within the cylinder mounted on the one of the plurality of sample filter holding means, respectively.

9. The sample preparation apparatus as claimed in claim 8, wherein at least one of the ATP extractant spray means and reagent spray means comprises spray sensing means for detecting a state of spraying in the cylinders while spraying.

10. The sample preparation apparatus as claimed in claim 7, further comprising reagent supply means for supplying the reagent to the reagent spraying means.

11. The sample preparation apparatus as claimed in claim 7, further comprising suction means for securing the sample filters onto the plurality of sample filter holding means by suction.

12. A method for preparing plural sample filters for inspecting a specimen isolated on each of the plural sample filters, comprising the steps of:

providing a turntable having a plurality of sample filter holding devices each configured to hold a sample filter, an ATP etractant spraying device configured to spray an ATP extractant and a reagent spray device configured to spray a reagent;

inserting the sample filter onto one of the plurality of sample filter holding devices, detecting the sample filter on the one of the plurality of sample filter holding devices;

controlling at least the ATP etractant spraying device and the reagent spray device to spray the ATP extractant and reagent onto the sample filter, respectively, when the sample filter is detected; and removing the sample filter from the one of the plurality of sample filter holding devices.

13. The method as claimed in claim 12, wherein:

the providing step comprises providing a cylinder configured to be mounted onto a respective one of the plurality of holding devices and a sensor configured to sense a state of spraying within the cylinders to the ATP etractant spraying device and the reagent spray device, respectively; and the controlling step comprises controlling the ATP etractant spraying device and the reagent spray device to adjust the spraying based on the state of spraying within the cylinders sensed by the sensor.

* * * * *